United States Patent [19]
Wu et al.

[11] Patent Number: 5,356,634
[45] Date of Patent: Oct. 18, 1994

[54] CONTROLLED-RELEASE DELIVERY SYSTEM

[75] Inventors: Stephen H. Wu; Carol J. Greene, both of Kingsport; Shane K. Kirk, Church Hill; David S. Kashdan, Kingsport, all of Tenn.

[73] Assignee: Eastman Chemical Company, Kingsport, Tenn.

[21] Appl. No.: 975,758

[22] Filed: Nov. 13, 1992

[51] Int. Cl.$^5$ ............................................. A61K 9/20
[52] U.S. Cl. ................................. 424/464; 424/480; 424/482; 525/54.21; 527/311
[58] Field of Search .................. 424/464, 482, 480; 525/54.21; 527/311

[56] References Cited

U.S. PATENT DOCUMENTS

| | | | |
|---|---|---|---|
| 3,489,743 | 1/1970 | Crane | 260/225 |
| 4,775,536 | 10/1988 | Patell | 424/482 |
| 4,795,641 | 1/1989 | Kashdan | 424/438 |
| 4,960,814 | 10/1990 | Wu et al. | 524/312 |
| 5,025,004 | 6/1991 | Wu et al. | 424/482 |
| 5,217,720 | 6/1993 | Sekigawa et al. | 424/480 |

OTHER PUBLICATIONS

Aqueous Polymeric Coatings for Pharmaceutical Dosage Forms, McGinnity, Dekker, New York (1989), p. 81.

"Materials Used in the Film Coating of Oral Dosage Forms", Rowe, Florence, Blackwell Scientific Publications, p. 1, 1894.

Kirk-Othmer, Encyclopedia of Chemical Technology, Third Ed., vol. 5, pp. 118-143 (1979), John Wiley & Sons, New York, New York.

Encyclopedia of Polymer Science & Engineering, vol. 3, pp. 158-181 (1985), John Wiley & Sons, New York, New York.

Ullman's Encyclopedia of Industrial Chemistry, vol. A5, pp. 438-447 (1986) VCH Verlagsgesellsehaft Weinheim, Germany.

Encyclopedia of Pharmaceutical Technology, vol. 5, pp. 188-200, Marcel Dekker, Inc., N.Y.

Primary Examiner—Thurman K. Page
Assistant Examiner—William E. Benston, Jr.
Attorney, Agent, or Firm—Bernard J. Graves, Jr.

[57] ABSTRACT

Provided is a controlled-release system for delivery of bioactive materials such as medicaments, cosmetic ingredients and agrichemicals using cellulose acetate succinate or certain blends of cellulose acetate phthalate polymers as enteric coating materials. Also provided is a method for delivering active ingredients to animals utilizing the controlled-release system of the invention.

8 Claims, 18 Drawing Sheets

SUGAR BEADS COATED WITH C-A-S AND
EXTRACTED WITH pH 6.8 BUFFER
FOR 2 HOURS

SUGAR BEADS COATED WITH C-A-S AND
EXTRACTED WITH pH 6.8 BUFFER
FOR 2 HOURS

SURFACE & X-SECTION ANALYSIS OF EXTRACTED COATINGS

SURFACE & X-SECTION ANALYSIS OF EXTRACTED COATINGS

SURFACE & X-SECTION ANALYSIS OF EXTRACTED COATINGS

SURFACE & X-SECTION ANALYSIS OF EXTRACTED COATINGS

SUGAR BEADS COATED WITH C-A-P
AND EXTRACTED WITH
pH 6.8 BUFFER FOR 2 HOURS

SUGAR BEADS COATED WITH C-A-P
AND EXTRACTED WITH
pH 6.8 BUFFER FOR 2 HOURS

SUGAR BEADS COATED WITH C-A-P
AND EXTRACTED WITH
pH 6.8 BUFFER FOR 2 HOURS

SUGAR BEADS COATED WITH C-A-P
AND EXTRACTED WITH
pH 6.8 BUFFER FOR 2 HOURS

SURFACE & X-SECTION ANALYSIS OF EXTRACTED COATINGS

SURFACE & X-SECTION ANALYSIS OF EXTRACTED COATINGS

SURFACE & X-SECTION ANALYSIS OF
EXTRACTED COATINGS

SURFACE & X-SECTION ANALYSIS OF
EXTRACTED COATINGS

CONTROLLED-RELEASE DELIVERY SYSTEM

FIELD OF THE INVENTION

This invention relates to a controlled-release system for delivery of bioactive materials such as medicaments, cosmetic ingredients and agrichemicals. In particular, it relates to a delivery system employing pH-sensitive hydrogel materials to achieve a desirable release profile of the active ingredient in an environment according to its pH.

BACKGROUND OF THE INVENTION

Polymeric materials which are insoluble at low pH but soluble in high pH are well known for enteric coating applications for medicaments. The polymers commonly used for enteric coatings are cellulose acetate phthalate (C-A-P), hydroxypropyl methylcellulose phthalate (HPMCP), cellulose acetate trimellitate (C-A-T), and hydroxypropyl methylcellulose acetate succinate (HPMCAS). Polyvinyl acetate phthalate (PVAP) and acrylic resins such as copoly(methacrylic acid/ethyl acrylate 1:1) and copoly(methacrylic acid/methyl methacrylate 1:1, or 1:2) are also known for their applications as enteric coating polymers. (See for example, Aqueous Polymeric Coatings for Pharmaceutical Dosage Forms, by J. W. McGinnity, Marcel Dekker, New York (1989), p. 81.)

In C-A-P for example, the specific pH at which it begins to dissolve is about pH 6.5. The specific pH is dependent on the degree of acetyl and phthalyl substitutions. The rate of dissolution of these polymeric enteric coating materials in alkaline media, although dependent on the nature of the buffer ions present in the solution, is relatively rapid.

A chapter entitled "Materials used in the film coating of oral dosage forms" by R. C. Rowe in the book edited by A. T. Florence and published by Blackwell Scientific Publications, p. 1, 1894, provides the art in general for formulating a pharmaceutical coating.

The polymers for enteric coating applications can be blended with each other to give a desirable dissolution profile at certain pH values, or blended with neutral water-soluble, or water-insoluble polymers for designing a drug delivery system. U.S. Pat. No. 4,795,641 teaches the composition of polymer blends containing a minor amount of cellulose acetate and a major amount of C-A-P, C-A-T, and cellulose acetate succinate. The blends have reverse phase morphology, that is, the minor component forms a continuous phase. The blends are useful for zero order controlled delivery of bioactive agents such as pharmaceutical agents and agricultural chemicals.

U.S. Pat. No. 3,489,743 describes a process for making cellulose mixed esters containing acetyl and phthalyl or hexahydrophthalyl moieties.

U.S. Pat. No. 4,960,814 describes water dispersible polymeric compositions based on polymers such as cellulose acetate phthalate.

Kirk-Othmer, Encyclopedia of Chemical Technology, Third Edition, Volume 5, pp. 118-143 (1979), John Wiley and Sons, New York, N.Y.; Encyclopedia of Polymer Science and Engineering, Volume 3, pp 158-181 (1985) John Wiley and Sons, New York, N.Y.; and Ullman's Encyclopedia of Industrial Chemistry, Fifth Completely Revised Edition, Volume A5, pp 438-447 (1986) VCH Verlagsgesellsehaft, Weinheim, Germany, provide general background information on cellulose ester technology.

SUMMARY OF THE INVENTION

Figure 1:
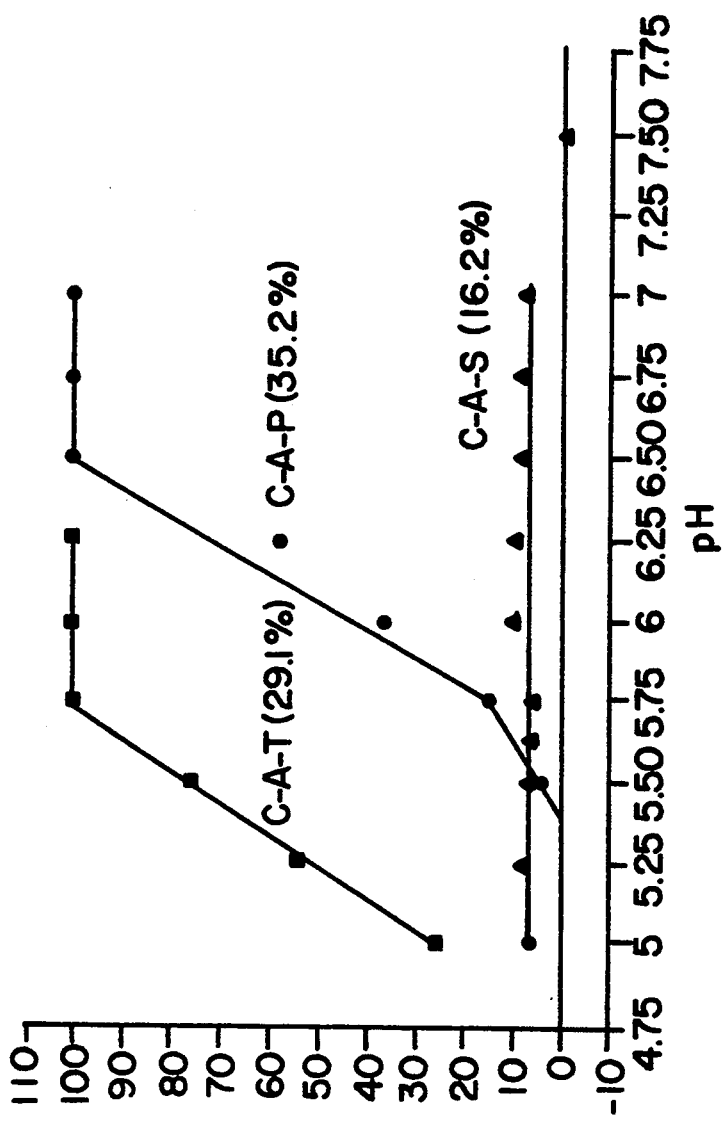
FIG. 1 illustrates the dissolution properties of C-A-T, C-A-P, and C-A-S films.

The present invention provides certain cellulose ester compositions which swell and form a gel in basic media such as in gastrointestinal fluids. The cellulose ester compositions of the present invention are useful as coatings for granulated or tabletted medicaments which allow the slow release of such bioactive materials.

DETAILED DESCRIPTION OF THE INVENTION

In accordance with this invention, it was discovered that C-A-S does not dissolve as rapidly in basic media as C-A-P and C-A-T, but rather forms a gel in basic media. The degree of gelation is pH-dependent. It was discovered that C-A-S has apparently the same acidic strength, but is not readily soluble in basic solution.

Thus, the present invention provides an enteric coating composition comprising a cellulose acetate succinate composition having an acetyl value of about 10 to 45%, a succinyl value of about 10 to 25%, and hydroxyl value of about 0.5 to 5%, an inherent viscosity of about 0.3-1.0 g/dL, and a molecular weight of about 15,000 to 75,000. They have inherent viscosities (determined in acetone) of about 0.3-1.0 g/dL. In this composition, it is preferred that the succinyl value is about 16 to 21 percent, most preferably about 17 weight percent.

It was also discovered that certain blends of cellulose acetate phthalate polymers (having phthalyl values ranging from about 15 to about 25%) with either cellulose acetate phthalate polymers (having phthalyl values ranging from about 10 to about 40%, preferably 28 to 40%) or cellulose acetate trimellitate polymers (having trimellityl values of about 15 to about 27%, with 17 to 25% being preferred) also provide gels when treated with a simulated gastrointestinal solution.

Thus, the present invention provides an enteric coating composition, comprising a blend of (a) a cellulose acetate phthalate polymer having phthalyl values ranging from about 15 to 25%, an inherent viscosity of about 0.3 - 1.0 g/dL, and a molecular weight of about 15,000 to 75,000; and (b) a cellulose acetate phthalate polymer having phthalyl values ranging from about 10 to about 40%.

In a preferred embodiment of this aspect of the present invention, the component (b) cellulose acetate phthalate polymer has phthalyl values ranging from about 28–40%.

As a further aspect of the present invention, there is provided an enteric coating composition, comprising a blend of (a) a cellulose acetate phthalate polymer having phthalyl values ranging from about 15–25%, an inherent viscosity of about 0.3–1.0 g/dL, and a molecular weight of about 15,000 to 75,000; and (b) a cellulose acetate trimellitate polymer having trimellityl content of about 15 to 27 weight percent.

The desired cellulose acetate succinate, cellulose acetate phthalate, and cellulose acetate trimellitate polymers are readily prepared using methods well known in the art.

Enteric coatings made with these polymers may also contain additives, pigments, colorants stabilizers, antioxidants, waxes and the like as desired.

In such solid dosage forms, it is preferred that the composition further comprises up to 15 weight percent of at least one coating additive, preferably about 10 to 25 weight percent, based on the total weight of the composition.

Commonly used coating additives include plasticizers such as dimethyl phthalate, diethyl phthalate, dioctyl phthalate, a monoglyceride, or triacetin; water-soluble polymers; annealing agents; pharmaceutical clays; colorants; additional surfactants such as TWEEN 80; thickening agents; and the like.

If the coating polymers exhibit acidic or basic functional groups, it is especially preferred to add a small amount of bases or acids, appropriately, as annealing agents to the coating dopes to partially neutralize the respective coating polymers, while still maintaining the integrity of the composition, so as to enhance the coalescing effect in the film-forming process on the surface of a substrate. A preferred amount of base is about 5% to about 50% equivalent of acid functional groups and a preferred amount of acid is about 5% to about 50% equivalent of basic functional groups. Typical bases inclued hydroxides such as NH$_4$OH, NaOH, and KOH; typical acids include acetic acid and hydrochloric acid.

Typical active ingredients include but are not limited to typical medicaments used in the art, such as adrenal cortical steroid inhibitors, analgesics (including aspirin, acetominophen, ibuprofen, codeine, morphine, and opium derivatives and other morphinans), anorexics (including amphetamine and non-amphetamine preparations), anti-alcohol preparations, antiarthritics (including anti-gout preparations), antiinfective drugs (i.e., erythromycin, cephalexin, cefaclor, ampicillin, amoxacillin, and the like), antiviral agents, anti-protozoal agents, anthelmintic agents, adrenergic blocking drugs including alpha- and beta-blocking agents, and the like.

The compositions of the present invention can be used to coat such active ingredients, preferably in tablet form, by methodology known in the art. Typical coating methods for applying enteric polymers are fluidized bed and side vented pan coating processes. In these processes, a coating formulation containing the enteric polymer and possibly other materials such as plasticizers and fillers are applied via spray nozzles onto the active ingredient. The active ingredient, usually in a tablet or bead from, is fluidized with heated gas or agitated by a rotating pan with heated gas while applying the coating to prevent agglomeration and in order to dry the polymer film. Both processes result in a uniform film being applied to the surface of the active ingredient. The release of the active ingredient is controlled by the coating thickness, additives in the coating, and the solubility of the active ingredient.

Thus, as a further aspect of the present invention, there is provided an active ingredient or medicament in granular or tabletted form, coated with the compositions of the present invention.

Alternatively, the compositions of the present invention can be used to produce a matrix-type dosage form. In matrix form, an active ingredient is dispersed within the hydrogel material and the release rate is thus dependent upon the rate that the gel forms and dissolves, the level of active ingredient relative to hydrogel material, and the solubility of the active ingredient. A matrix type dosage form can be prepared by dispersing the active ingredient in the polymer solution and removing the solvent to produce a film, by extrusion of the polymer/active ingredient mixture, or by granulation of the active ingredient using a polymer solution.

As a further aspect of the present invention, there is provided a method for treating an animal in need of such treatment comprising administering to said animal a biologically-effective amount of a composition comprising an active ingredient in tablet or granular form, coated with an enteric coating composition comprising a cellulose acetate succinate composition having an acetyl value of about 10 to 45%, a succinyl value of about 10 to 25%, and hydroxyl value of about 0.5 to 5%, an inherent viscosity of about 0.3–1.0 g/dL, and a molecular weight of about 15,000 to 75,000.

Also provided by the present invention is the above method wherein the composition is an enteric coating composition, comprising either a blend of (a) a cellulose acetate phthalate polymer having phthalyl values ranging from about 15–25%, an inherent viscosity of about 0.3–1.0 g/dL, and a molecular weight of about 15,000 to 75,000; and (b) a cellulose acetate trimellitate polymer having trimellityl values of about 15–27%; or a blend of (a) a cellulose acetate phthalate polymer having phthalyl values ranging from about 15 to 25%, an inherent viscosity of about 0.3–1.0 g/dL, and a molecular weight of about 15,000 to 75,000; and (b) a cellulose acetate phthalate polymer having phthalyl values ranging from about 10 to about 40%.

In the method for treating animals, the solid dosage form is preferably administered orally. The solid dosage form contains an effective amount of medicament which is that amount typically used in the art to render a desired treatment. This amount will vary greatly depending upon the nature of the medicament and the desired type of treatment. "Treatment" refers to any desired purpose for administering a medicament such as prevention, control, or cure of a disease; maintaining or improving the health of an animal; increasing weight gain or feed conversion of a farm animal; and the like.

EXPERIMENTAL SECTION

EXAMPLE 1

This example shows the pH-dependent dissolution characteristics of the polymeric films.

The dissolution properties of C-A-P, C-A-T, and C-A-S films are determined by the weight loss of a piece of polymeric film (1 cm×1 cm×0.1 mm) immersed in simulated gastric fluid at pH 1.2 for 90 min. and then extracted in 0.1M phosphate buffers at pH 5.0–7.5 for three hours. These in vitro conditions are used to simulate the gastrointestinal environment and the residence times of a dosage form in the gastrointestinal tract. The films are prepared by casting the acetone solution of a polymer on a glass plate. The dissolution properties of C-A-T, C-A-P, and C-A-S films are shown in FIG. 1. C-A-T exhibits a characteristic pH range for the onset and completion of film dissolution lower than C-A-P. It is extremely interesting to see that C-A-S film does not dissolve, but only swells under the experimental conditions.

EXAMPLE 2

This example illustrates the pH-dependent swelling characteristics of C-A-S.

Figure 2:
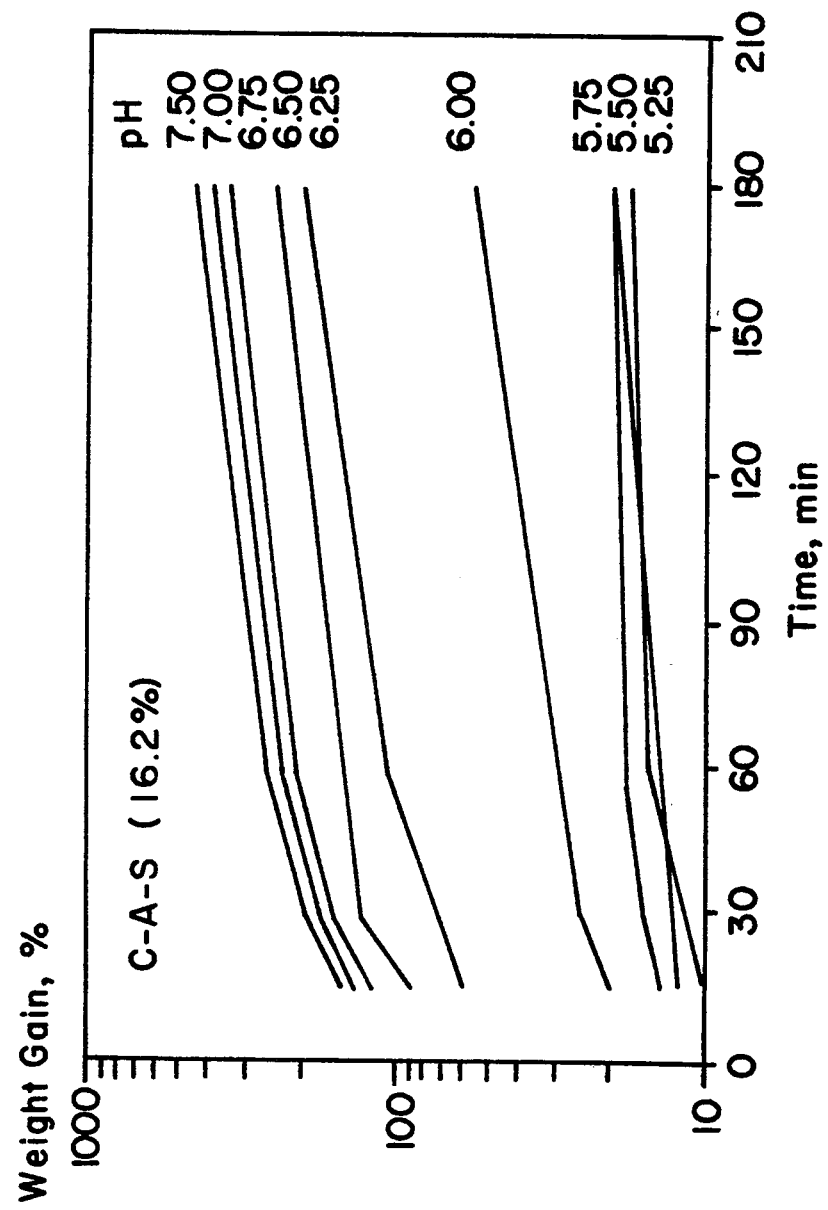
FIG. 2 shows the swelling characteristics of C-A-S film in various buffers as a function of time.

The pH-dependent swelling characteristics of C-A-S are determined by the weight gain of a polymeric film in buffers as a function of time and temperature. Thus the swelling characteristics of C-A-S film in various buffers as a function of time is shown in FIG. 2. C-A-S may be viewed as a pH-sensitive hydrogel material. These unusual properties of C-A--S as shown in Example 1 and 2 form the basis for the disclosed invention.

EXAMPLE 3

This example illustrates the pH-dependent swelling characteristic of C-A-S by examining the morphological properties of the film coated onto sugar beads, and the application of this characteristic on release of active drugs from the coated beads.

Sugar beads (−14/+16 mesh, U.S. standard), which are commonly used as a placebo for depositing drugs onto the surface and then coated with a membrane layer to formulate a multiple dosage form, are coated with enteric polymers, or blends of enteric polymers. Coated beads are then extracted in simulated intestinal fluid which has a pH value of 6.8 for a period of 0.5, 1.0, 2.0, and 3.0 hrs. The morphology of the cross sections of the swollen coatings on sugar beads are examined by scanning electron microscopy. Typical scanning electron micrographs are shown in FIG. 3.

Figure 3:
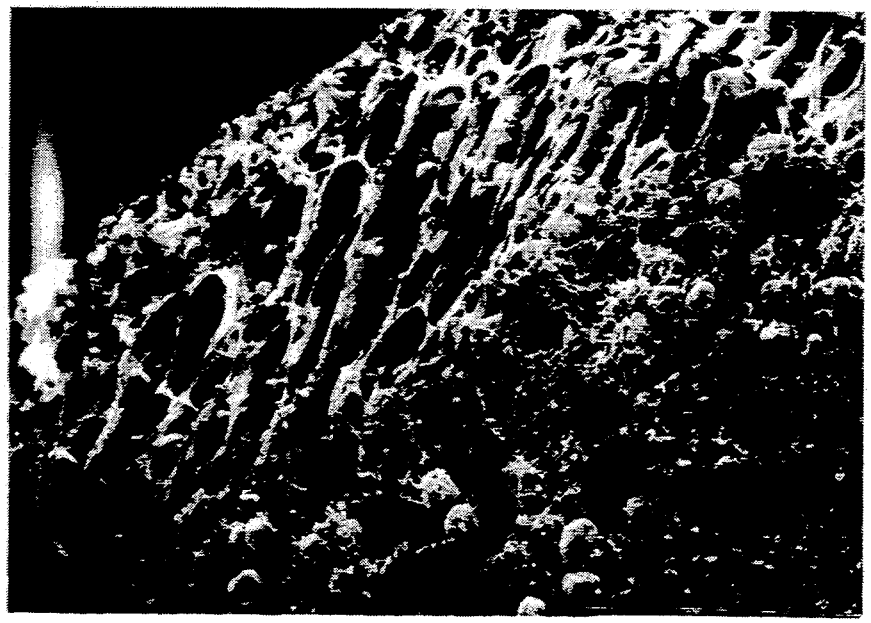
FIGS. 3 and 4 show the morphology of C-A-S by scanning electron microscopy (SEM).
Figure 4:
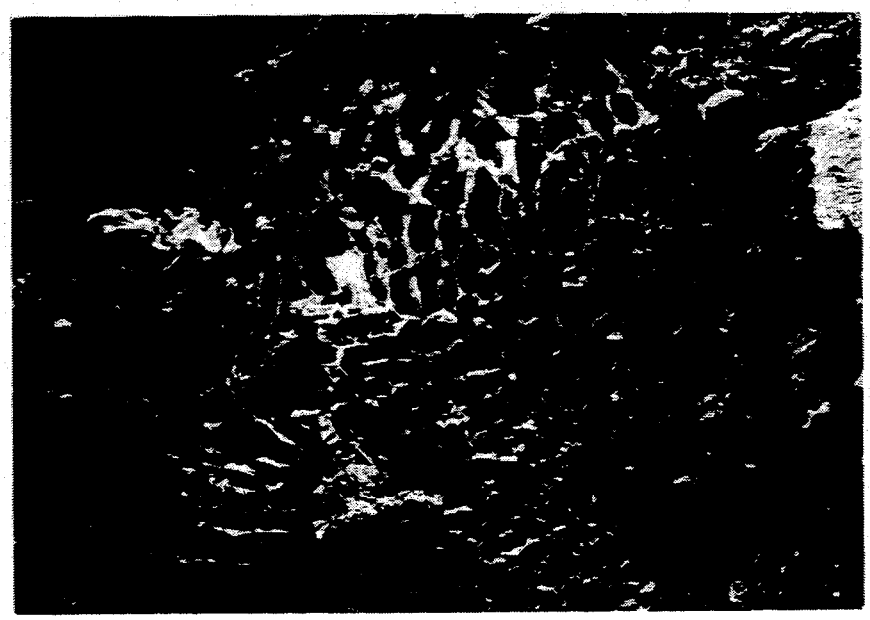
Figure 5:
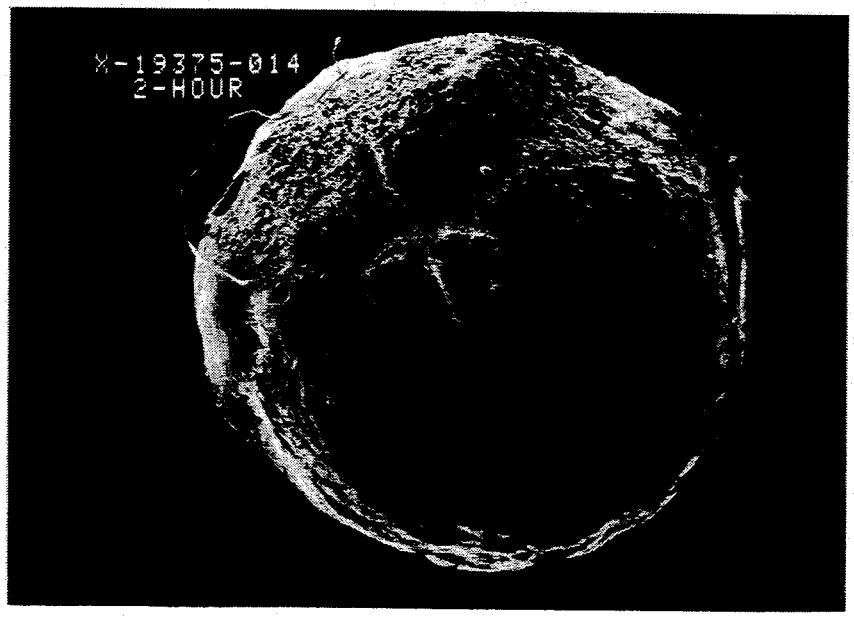
FIGS. 5, 6, 7, and 8 show SEM of C-A-S after a period of extraction of 0.5 to 2 hours in a simulated intestinal fluid.
Figure 6:
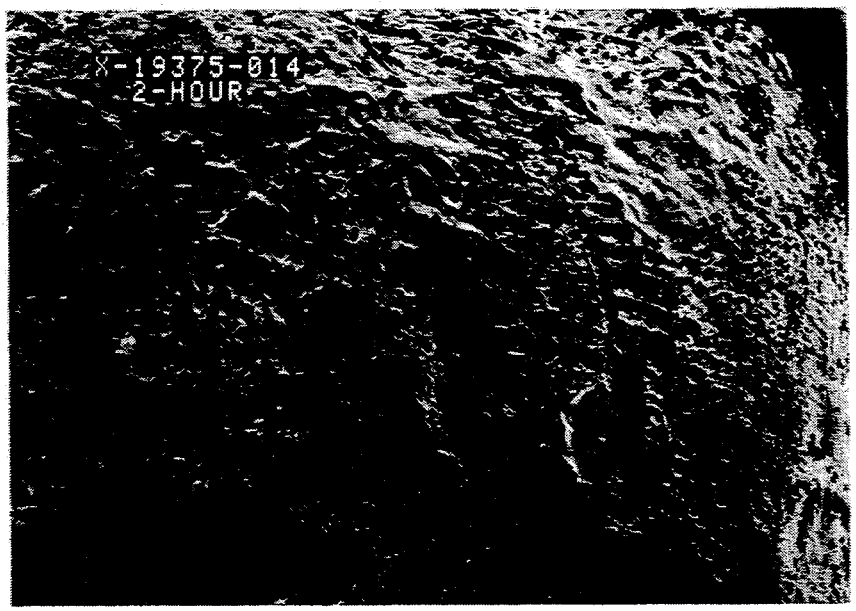

A study of SEM micrographs indicates that C-A--S (17%S) exhibits a unique swollen gel structure in the simulated intestinal fluid at pH 6.8 after two hours of extraction (FIG. 3). C-A-T quickly dissolves, and no coating is left on the beads after two hours. Ethylcellulose, a neutral pH-independent polymer, does not exhibit the sponge-like network. The coating thickness remains essentially the same after a period of extraction time from 0.5 to 2 hours (FIG. 4). C-A-P (36%P) does not exhibit the sponge-like network after extraction. The decrease of the coating thickness after a period of extraction time from 0.5 to 3.0 hrs indicated quick erosion from the outer surface which was in contact with the simulated intestinal fluid (FIG. 5). Similarly a blend of C-A-P (36%P) and C-A-T (26%T) does not show the sponge-like structure after extraction. The coating of a blend of C-A-S (17%S)/C-A-P (36%P)/C-A-T (26%T) (1:1:1) gives the sponge-like network, and the thickness of the sponge-like network increases as the extraction time is prolonged (FIG. 6).

These observations clearly show that the sponge-like network provide a swollen gel layer on the surface of sugar beads so as to slow down the diffusion or migration of drug molecules to the bulk fluid.

Figure 7:
Figure 8:
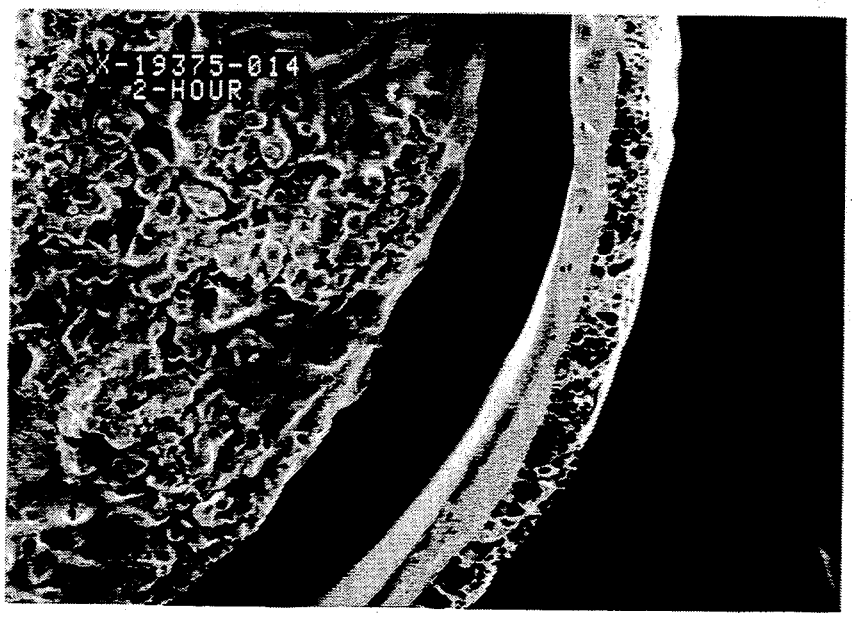
Figure 9:
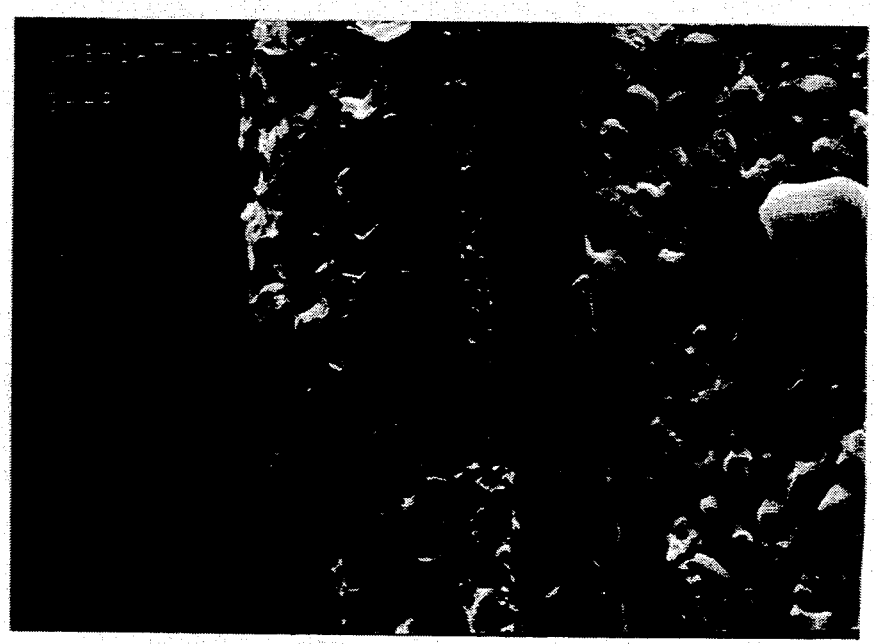
FIGS. 9 and 10 show SEM of C-A-S after a period of extraction of from 0.5 to 3 hours in a simulated intestinal fluid.
Figure 10:
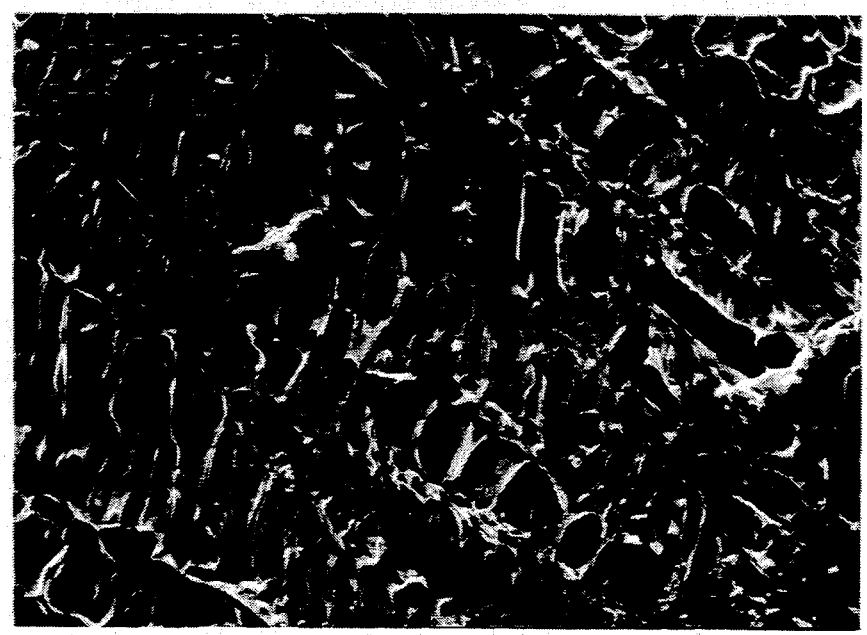
Figure 11:
FIGS. 11, 12, 13, and 14 show that the coating of a blend of C-A-S (17%S)/C-A-P (36%P)/C-A-T (26%T) (1:1:1) gives the sponge-like network, and the thickness of the sponge-like network increases as the extraction time is prolonged.
Figure 12:
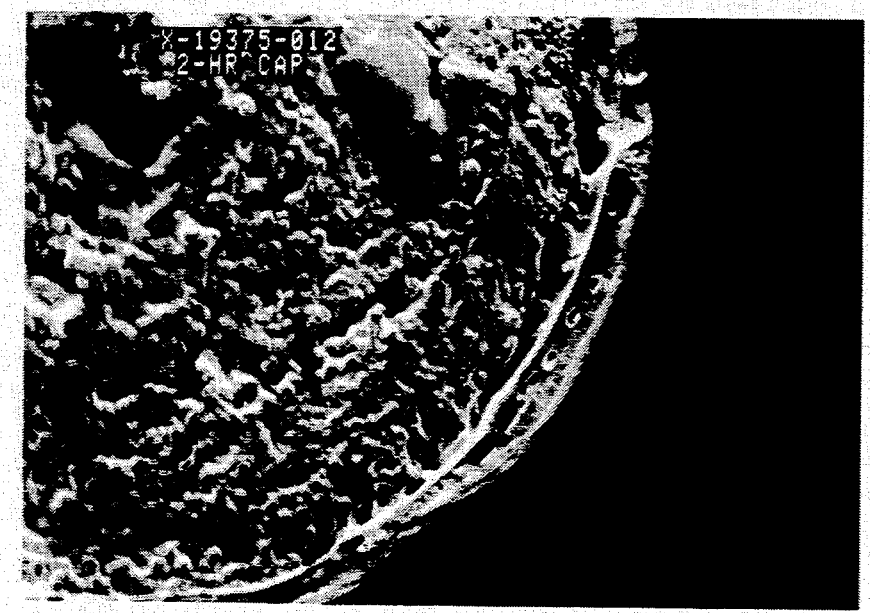
Figure 13:
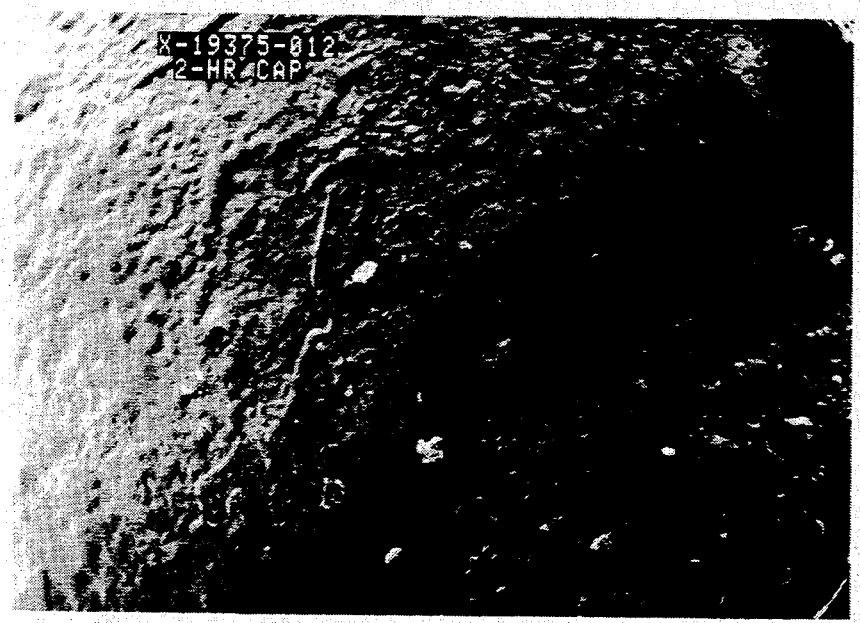
Figure 14:
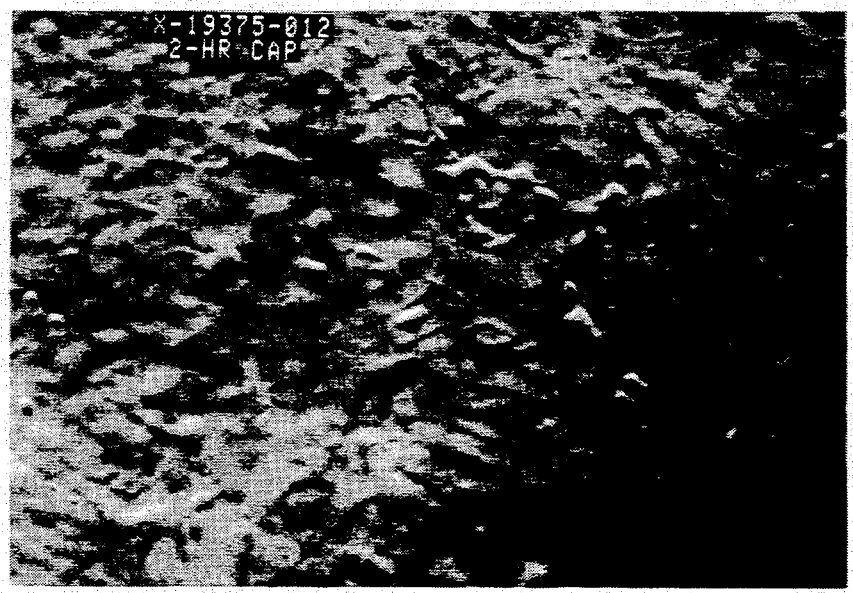
Figure 15:
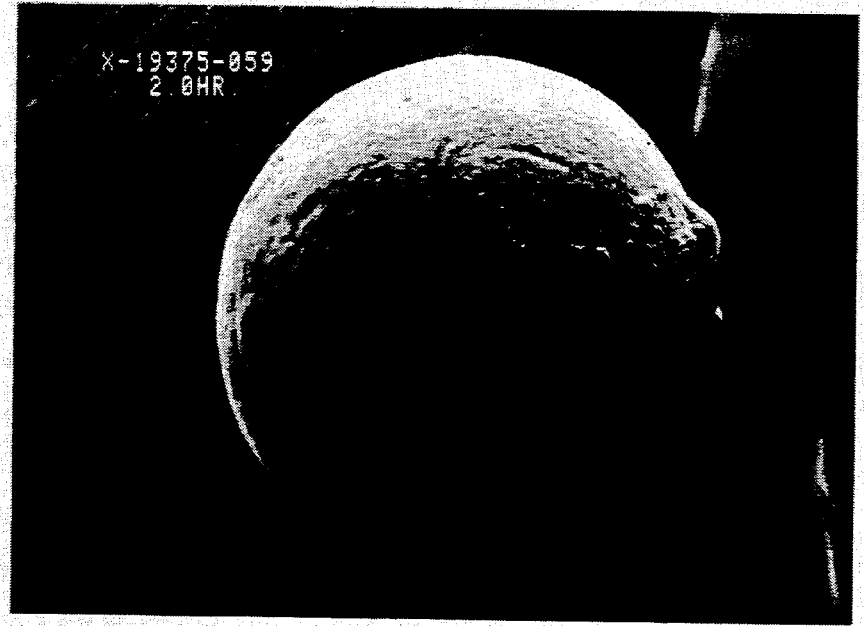
FIGS. 15, 16, 17, and 18 show the morphology of a blend of C-A-P (18% phthalyl substitution) with C-A-P having higher phthalyl content. Such blends (1.3 by weight ratio) provide coatings with a sponge-like structure similar to those made with C-A-S when soaked in simulated intestinal fluid. Sugar beads are coated with the following coatings and then extracted in simulated intestinal fluid as described in Example 1 below.
Figure 16:
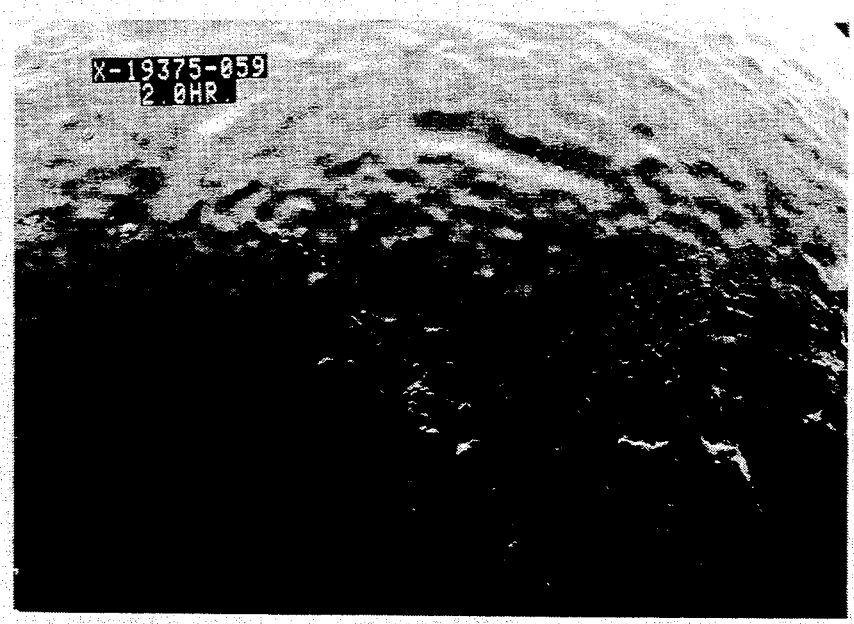
Figure 17:
Figure 18:

This example illustrates the unexpected results obtained with blend of C-A-P (18% phthalyl substitution) with C-A-P having higher phthalyl content. Such blends (1.3 by weight ratio) provide coatings with a sponge-like structure similar to those made with C-A-S when soaked in simulated intestinal fluid. Sugar beads are coated with the following coatings and then extracted in simulated intestinal fluid as described in Example 1. The spong-like morphological structure is showin in FIG. 7.

These observations show that C-A-P with a low phthalyl content may be blended with other enteric polymers to slow down or inhibit the erosion of C-A-P coating.

EXAMPLE 5

Methionine pellets are coated with a coating composition consisting of C-A-P (36% phthalyl substitution) and triacetin (9:1), and another coating consisting of a blend of C-A-P (18%P)/C-A-P (36%), 1:3 and triacetin. Coated pellets were extracted with pH 6.8 simulated intestinal fluid at 37° C. The release profiles are shown as follows:

| Time | Methinoine Release, % of Total | |
|---|---|---|
| | C-A-P (36% P) | C-A-P (18% P)/C-A-P (36% P (1:3) |
| 5 min | 30.0 | 0.0 |
| 15 min | 52.0 | 17.5 |
| 30 min | 71.0 | 47.0 |
| 60 min | 88.0 | 80.0 |

| COATING COMPOSTION | EXTRACTION TIME (HRS) | COATING MORPHOLOGY |
|---|---|---|
| 1. C-A-S (17% S), 4% on beads | 2.0 | Sponge-like network. |
| 2. C-A-T (26% T), 4% on beads | 2.0 | coating dissolved. |
| 3. Ethylcellulose, 4% | 0.5, 1.0, 2.0 | Band-like structure; no decrease in thickness. |
| 4. C-A-P (36% P), 4% | 0.5, 1.0, 2.0, 3.0 | Band-like structure; decrease in thickness. |
| 5. C-A-P (36% P)/C-A-T (26% T), (1:1), 4% | 2.0 | No sponge-like network observed. |
| 6. C-A-S/C-A-P/C-A-T (1:1:1), 4% | 0.5, 1.0, 2.0, 3.0 | sponge-like network. |

This example shows that the blend exhibit a slower release profile.

We claim:

1. An enteric coating composition, comprising a blend of
   (a) a cellulose acetate phthalate polymer having phthalyl values ranging from about 15 to 25%, an inherent viscosity of about 0.3–1.0 g/dL, and a molecular weight of about 15,000 to 75,000; and
   (b) a cellulose acetate phthalate polymer having phthalyl values ranging from about 10 to about 40%.

2. The composition of claim 1, wherein the component (b) cellulose acetate phthalate polymer has phthalyl values ranging from about 28 to 40%.

3. An enteric coating composition, comprising a blend of
   (a) a cellulose acetate phthalate polymer having phthalyl values ranging from about 15–25%, an inherent viscosity of about 0.3–1.0 g/dL, and a molecular weight of about 15,000 to 75,000; and
   (b) a cellulose acetate trimellitate polymer having trimellityl values of about 15–27%.

4. The composition of claim 3, wherein the cellulose acetate trimellitate polymer has a trimellityl values of about 17–25%.

5. A method for treating an animal in need of such treatment comprising administering to said animal a biologically-effective amount of a composition comprising an active ingredient in tablet or granular form, coated with an enteric coating composition, comprising a blend of
   (a) a cellulose acetate phthalate polymer having phthalyl values ranging from about 15 to 25%, an inherent viscosity of about 0.3–1.0 g/dL, and a molecular weight of about 15,000 to 75,000; and
   (b) a cellulose acetate phthalate polymer having phthalyl values ranging from about 28 to about 40%.

6. A method for treating an animal in need of such treatment comprising administering to said animal a biologically-effective amount of a composition comprising an active ingredient in tablet or granular form, coated with an enteric coating composition, comprising a blend of
   (a) a cellulose acetate phthalate polymer having phthalyl values ranging from about 15–25%, an inherent viscosity of about 0.3–1.0 g/dL, and a molecular weight of about 15,000 to 75,000; and
   (b) a cellulose acetate trimellitate polymer having trimellityl values of about 15–27%.

7. A medicament in tablet or granular form coated with the enteric coating composition of claim 1.

8. A medicament in tablet or granular form coated with the enteric coating composition of claim 3.

* * * * *